(12) United States Patent
Wegener et al.

(10) Patent No.: US 10,400,216 B2
(45) Date of Patent: Sep. 3, 2019

(54) METHODS FOR CELL WASHING WITH ON-LINE DILUTION OF CELL FEED

(71) Applicant: Fenwal, Inc., Lake Zurich, IL (US)

(72) Inventors: Christopher J. Wegener, Libertyville, IL (US); Daniel R. Boggs, Libertyville, IL (US); Bret M. Olson, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 44 days.

(21) Appl. No.: 14/574,539

(22) Filed: Dec. 18, 2014

(65) Prior Publication Data

US 2016/0177262 A1     Jun. 23, 2016

(51) Int. Cl.
*A61M 1/02*     (2006.01)
*A61M 1/26*     (2006.01)
(Continued)

(52) U.S. Cl.
CPC ......... *C12N 5/0641* (2013.01); *A61M 1/0209* (2013.01); *A61M 1/0218* (2014.02); *A61M 1/0236* (2014.02); *A61M 1/265* (2014.02); *A61M 1/34* (2013.01); *B01D 61/00* (2013.01); *B01D 61/18* (2013.01); *B01D 63/062* (2013.01);
(Continued)

(58) Field of Classification Search
CPC ...... B01D 63/16; B01D 63/065; B01D 61/00; B01D 2315/02; B01D 61/18; B01D 63/062; B01D 71/40; B01D 71/50; B01D 2311/04; A61M 1/0209; A61M 1/0265; A61M 1/0218; A61M 1/0236; A61M 1/34;
(Continued)

(56) References Cited

U.S. PATENT DOCUMENTS 5,034,135 A * 7/1991 Fischel ............... A61M 1/3696
                                                210/321.68
5,194,145 A * 3/1993 Schoendorfer ..... A61M 1/3496
                                                210/321.63
(Continued)

FOREIGN PATENT DOCUMENTS

WO    WO2012125457 A1    9/2012
WO    WO2014039086 A1    3/2014

OTHER PUBLICATIONS

Schoendorfer, D. W. "Automation in Apheresis." Automation in Blood Transfusion. Eds. C. Th. Smit Sibinga et al. New York: Springer Science + Business Media, 1989. 129-146.*

(Continued)

*Primary Examiner* — Benjamin L Lebron
(74) *Attorney, Agent, or Firm* — Cook Alex Ltd.

(57) ABSTRACT

Systems and methods for the washing of biological fluid/biological cells are disclosed. The method provides for the automated dilution of the cell feed during the cell washing procedure using a separator in which the separator has a predetermined maximum output concentration for the biological cells that are being washed. The method further includes determining the concentration ratio of the biological cells to be washed in the washing procedure and determining a maximum input concentration as a function of the maximum output concentration and the concentration ratio. Wash solution is then added to dilute said biological cells so that the maximum input concentration of the diluted biological cells entering the separator is not exceeded.

15 Claims, 4 Drawing Sheets

(51) Int. Cl.
*A61M 1/34* (2006.01)
*A61M 1/36* (2006.01)
*B01D 61/00* (2006.01)
*B01D 61/18* (2006.01)
*B01D 63/06* (2006.01)
*B01D 63/16* (2006.01)
*B01D 71/50* (2006.01)
*C12N 5/078* (2010.01)
*B01D 71/40* (2006.01)

(52) U.S. Cl.
CPC .......... *B01D 63/065* (2013.01); *B01D 63/16* (2013.01); *B01D 71/50* (2013.01); *A61M 1/3692* (2014.02); *A61M 2202/0429* (2013.01); *A61M 2202/0439* (2013.01); *B01D 71/40* (2013.01); *B01D 2311/04* (2013.01); *B01D 2315/02* (2013.01)

(58) Field of Classification Search
CPC ................ A61M 1/3692; A61M 1/265; A61M 2202/0429; A61M 2202/0439; C12N 5/0641
See application file for complete search history.

(56) References Cited

U.S. PATENT DOCUMENTS

| | | | | |
|---|---|---|---|---|
| 5,783,085 | A | * | 7/1998 | Fischel ............... A61M 1/3696 210/321.68 |
| 6,045,701 | A | * | 4/2000 | Ung-Chhun ........ A61M 1/3679 210/321.67 |
| 8,071,282 | B2 | * | 12/2011 | Bitensky .................. A01N 1/02 435/2 |
| 2002/0033367 | A1 | * | 3/2002 | Prince ................ B01D 39/1692 210/650 |
| 2013/0005558 | A1 | * | 1/2013 | Inadome ............. A61M 1/0209 494/36 |
| 2013/0092630 | A1 | | 4/2013 | Wegener |

OTHER PUBLICATIONS

European Search Report and Search Opinion, counterpart International Appl. EP Appl. No. 15200438, dated Mar. 11, 2016.

* cited by examiner

METHODS FOR CELL WASHING WITH ON-LINE DILUTION OF CELL FEED

CROSS-REFERENCE TO RELATED APPLICATIONS

Technical Field

The present disclosure is generally directed to methods for washing biological cells. More particularly, the present disclosure is directed to the sterile sequential processing of biological fluid and washing of biological cells using a disposable fluid circuit and a reusable processing apparatus in a closed system or environment. The present disclosure is also directed to systems and method for washing biological cells with on-line dilution of the cell feed.

Background

The processing of biological fluid such as blood or blood components typically involves using a reusable processing apparatus ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

The disposable fluid circuits typically include plastic containers and tubes that are pre-connected, pre-assembled, and pre-sterilized, such as by radiation or steam sterilization. In some processing systems and methods, containers including liquids such as anticoagulant, saline, wash solution, storage media, or treating agents may likewise be pre-attached to the disposable fluid circuit, thereby creating a "closed" system. A "closed" system is one where the interior of the system, i.e., internal flow paths, separation chambers, etc., are not exposed or "opened" to the outside environment.

Where the biological cells are separated using a separation membrane, such as, but not limited to, a spinning membrane, the systems utilizing such membranes may on occasion be subject to increases in pressure. Certain increases in pressure may be caused by the build-up of cellular material at the membrane surface, leading to a reduced yield of the target cells. Thus, it would be desirable to provide a system that prevents inadvertent target cell loss.

SUMMARY

In one aspect, the present disclosure is directed to a method for washing biological cells. In the illustrated embodiment, the method utilizes a separator that includes a relatively rotatable cylindrical housing and an internal member wherein the cylindrical housing has an interior surface and the internal member has an exterior surface. The surfaces define a gap therebetween wherein at least one of the surfaces includes a porous membrane.

The separator has a predetermined maximum output concentration for the biological cells that are being washed. The method further includes determining a concentration ratio of the biological cells to be washed in the washing procedure and determining a maximum input concentration as a function of the maximum output concentration and the concentration ratio. The biological cells to be washed are drawn from a container in flow communication with the separator, and wash solution is added to dilute said biological cells so that the maximum input concentration of the diluted biological cells entering the separator is not exceeded.

The method may further include introducing diluted cells into the gap of the separator, rotating at least one or both of the housing and the internal member and separating the cells from the liquid medium to concentrate the cells. At least some of the concentrated cells are removed from the separator through a first outlet, and at least some of the separated liquid medium is removed from the separated through a second outlet.

Other aspects of the method include empirically deriving the maximum output concentration for the separator, and diluting the biological cells by either i) combining the biological cells with the wash solution and introducing the combination of cells and diluent into the separator, or ii) first introducing the wash solution into the separator followed by adding biological cells to the separator.

DETAILED DESCRIPTION

Systems and methods for the automated sequential sterile processing of biological fluid are disclosed herein. The systems disclosed typically include a reusable separation apparatus and one or more disposable processing circuits adapted for association with the reusable apparatus. The reusable separation apparatus may be any apparatus that can provide for the automated processing of biological fluid. By "automated," it is meant that the apparatus can be pre-programmed to carry out the processing steps of a biological fluid processing method without substantial operator involvement. Of course, even in the automated system of the present disclosure, it will be understood that some operator involvement will be required, including the loading of the disposable fluid circuits and entering processing parameters. Additional manual steps may be required as well. However, the reusable apparatus can be programmed to process biological fluid through each of the disposable circuits described below without substantial operator intervention.

Figure 3:
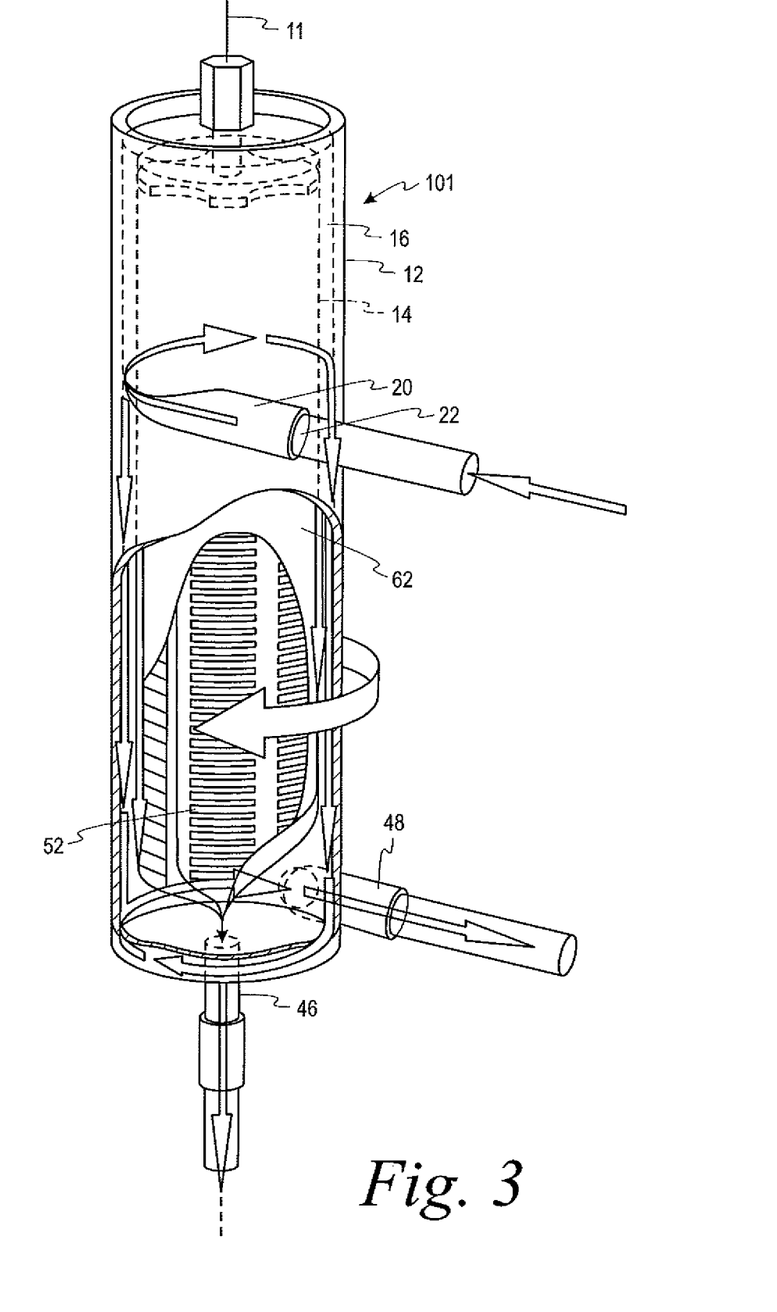
FIG. 3 is a perspective view of a separation/washing device using a spinning membrane.

The reusable processing apparatus is typically capable of effecting the separation of a biological fluid that includes biological cells into two or more components or fractions. Thus, the reusable apparatus may generate conditions which allow for the separation of a biological fluid into selected components or fractions. In accordance with the present disclosure, one preferred means for separating biological fluid into its constituent components or fractions is an apparatus that uses a spinning porous membrane to separate one component from other components. An example of such apparatus is the Autopheresis C® sold by Fenwal, Inc. of Lake Zurich, Ill. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which is also incorporated herein in its entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane covered spinner having an interior collection system disposed within a stationary shell. While a detailed discussion of the separation device is beyond the scope of this application, the spinning membrane separation device is shown in FIGS. 6, 7(a)-7(b) and is discussed below. In another embodiment, the reusable apparatus may generate a centrifugal field to effect separation.

Figure 1:
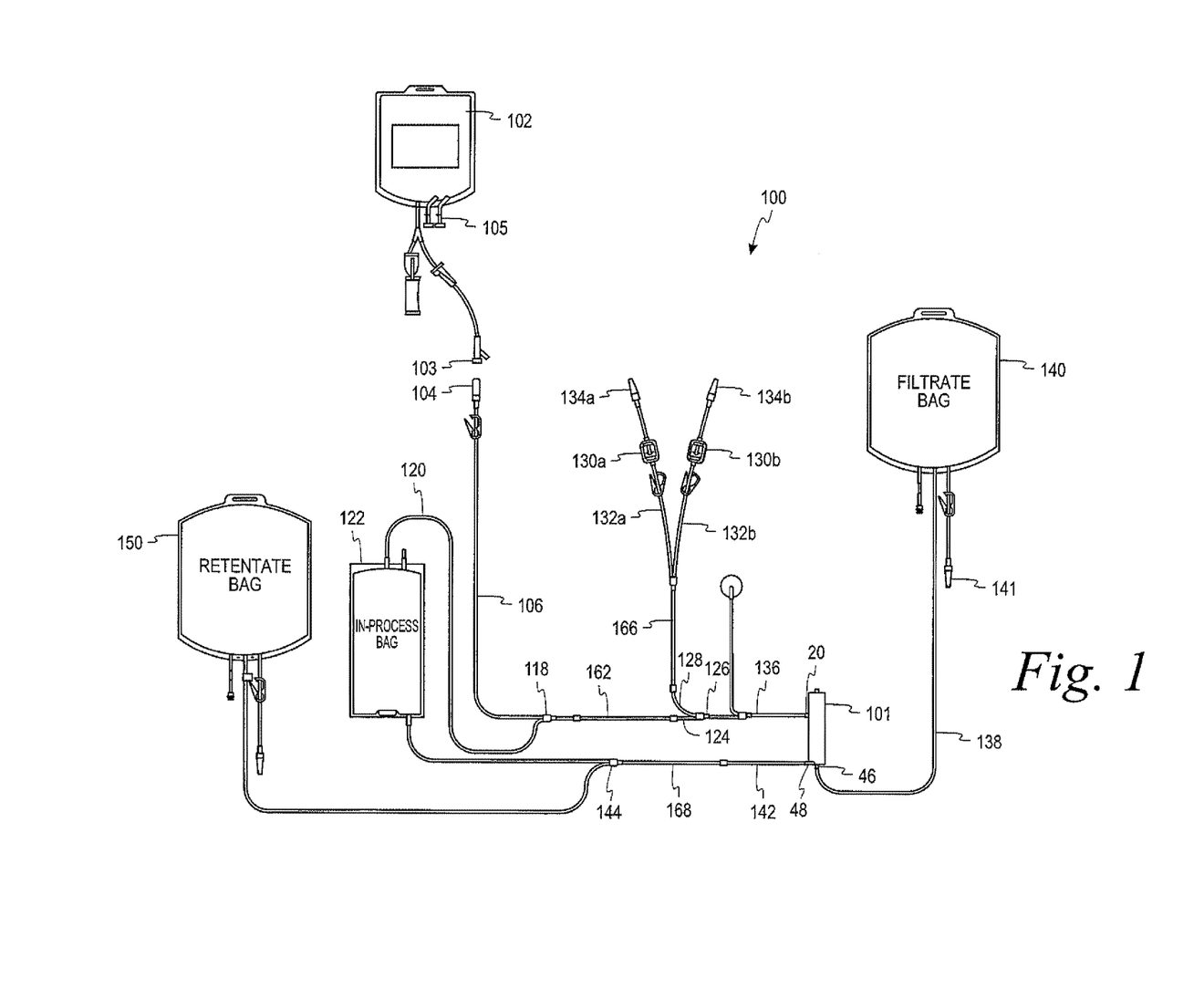
FIG. 1 is a schematic view of one embodiment of a disposable fluid circuit useful in the systems and methods described herein.

Turning now to FIG. 1, the systems described herein preferably include two or more disposable fluid circuits for use in the processing of biological fluid. While the circuits described herein may be used as stand-alone circuits, more preferably, at least two or more disposable fluid circuits are used in combination and in series for the separation, washing, volume reduction and/or other processing of a biological fluid. Circuit 100 may include an integrated separation device, such as, but not limited to, the spinning membrane 101 described above. Circuits 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in greater detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 1, the tubing of circuit 100 includes spaced tubing segments identified by reference numerals 162, 166, 168. The tubing segments are provided for mating engagement with the peristaltic pumps of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized polyvinyl chloride. Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 1 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 1, tubing segment 106 extends from docking site 104 and is connected to further downstream branched-connector 118. Branched-connector 118 communicates with tubing 106 and tubing 120, which provides a fluid flow path from "in-process" container 122, described in greater detail below. Tubing segment 124 extends from branched-connector 118 and is joined to a port of further downstream branched-connector 126. A separate flow path defined by tubing 128 is also connected to a port of branched-connector 126.

Figure 4:
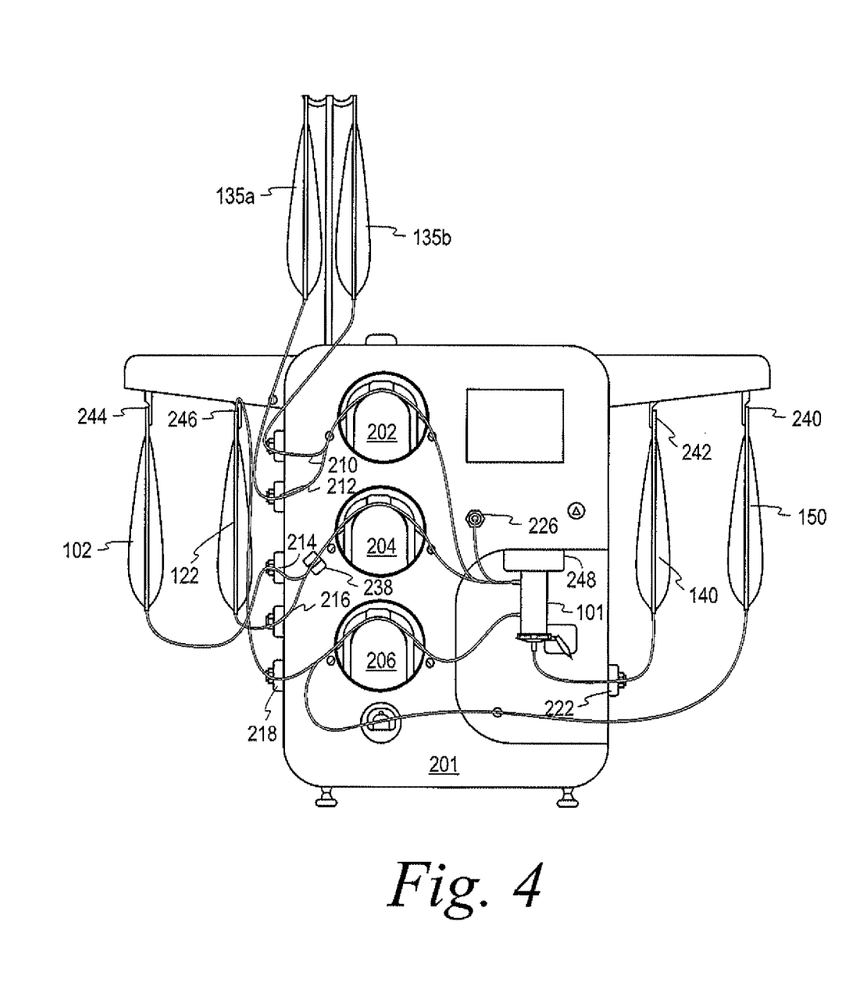
FIG. 4 is another view of the front panel of a reusable processing and/or cell washing apparatus with a disposable fluid circuit loaded thereon.

In accordance with the fluid circuit of FIG. 1, one or more containers of wash or other processing/treating solution may be attached (or pre-attached) to set 100. As shown in FIG. 1, tubings 132a, 132b (defining a flow path) preferably include and terminate in an access site such as spike connectors 134a, 134b. Access sites 134a, 134b are provided to establish flow communication with containers 135a, 135b (shown in FIG. 4) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 μm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 1 (and described in greater detail in connection with FIG. 3), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container includes a further connection port 141 for sampling or withdrawing the waste from within the product container.

Separation device 101 preferably includes a second outlet 48 that is connected to tubing segment 142 for directing the desired biological cell/fluid product to "final" product container. The other end of tubing segment 142 is connected to branched-connector 144, which branches into and defines a flow path to one or more in-process containers 122 and a flow path to a final product container 150. The final product container 150 may also include a sampling assembly (not shown).

Figure 2:
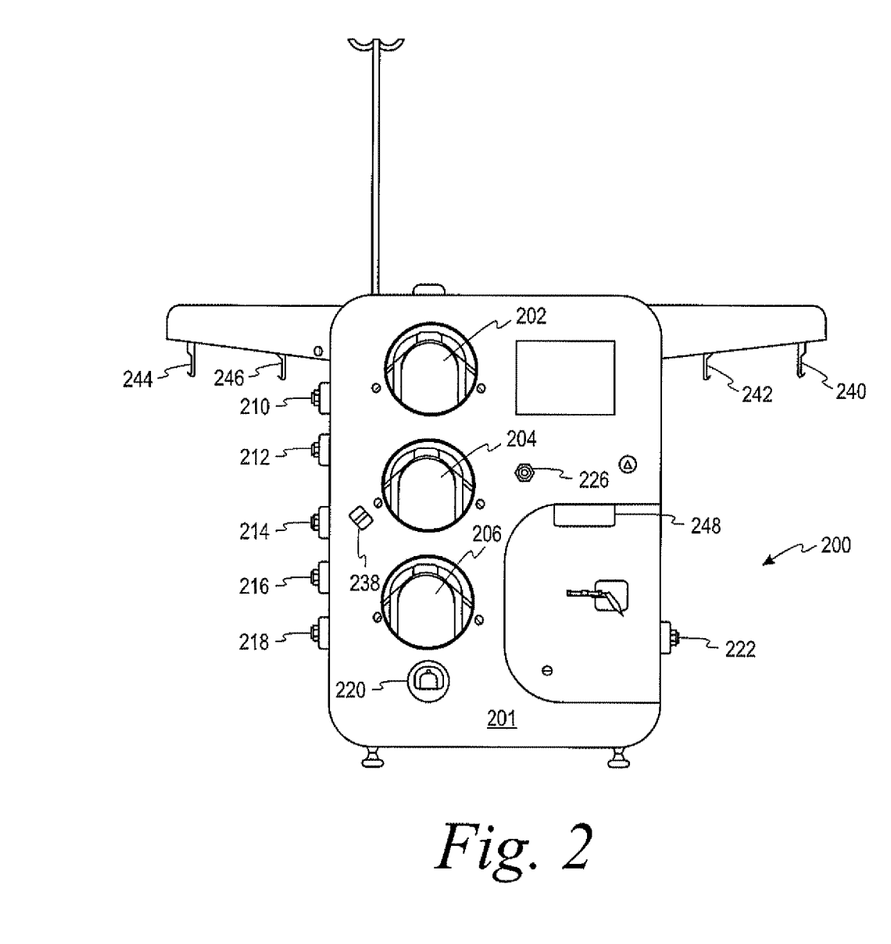
FIG. 2 is an enlarged view of the front panel of the reusable processing apparatus.

FIG. 2 shows the front panel 201 of reusable hardware processing apparatus 200. Apparatus 200 may be of compact size suitable for placement on a table top of a lab bench and adapted for easy transport. Alternatively, apparatus 200 may be supported by a pedestal that can be wheeled to its desired location. In any event, as shown in FIG. 2, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 1 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container, in-process container, source container, and any additional container(s), respectively, may depend and be weighed. The weights of the bags are monitored by weight sensors and recorded during a washing or other procedure. From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Turning to FIG. 3, a spinning membrane separation device, generally designated 101, is shown. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 3. The boundaries of the blood flow path are generally defined by gap 16 between the interior surface of housing 12 and the exterior surface of rotary spinner 14. The spacing between the housing and the spinner is sometimes referred to as the shear gap. In one non-limiting example, the shear gap may be approximately 0.025-0.050 inches (0.067-0.127 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.025 to about 0.075 inches (0.06-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in a outlet orifice 46 concentric with the central axis.

In the illustrated embodiment, the surface of the rotary spinner 14 is at least partially, and is preferably substantially or entirely, covered by a cylindrical porous membrane 62. The membrane 62 typically has a nominal pore size of 4.0 microns, but other pore sizes, for example, of from 0.8 microns to 30.0 microns, may alternatively be used. Membranes useful in the washing methods described herein may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 4.0 μm and a thickness of approximately 10 μm or greater. Membranes of this type will typically retain all cellular components (e.g., red blood cells, white blood cells) and certain formed blood components, e.g., platelets. In another embodiment, the membrane may be made of a thin (approximately 10-50 micron (μm) thick) sheet of, for example, polycarbonate. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

U.S. Patent Application Pub. No. US 2013/0092630, the contents of which is incorporated herein by reference, discloses methods and systems for washing biological cells using a reusable hardware apparatus and disposable fluid circuit including a spinning membrane separator. The methods disclosed therein involve the processing, washing, treating and incubating of biological cells, such as mononuclear cells for subsequent therapeutic administration. In keeping with the present disclosure, the systems and methods are in the context of the washing sub-procedure, and it will be understood that this sub-procedure is used in conjunction with processing, treating and incubating methods, such as those discussed in the referenced applications. However, the description below is not intended to limit the method or the use of the system and the fluid circuits described below.

Many of the steps of the method are similar to those described in U.S. Patent Application Pub. No. US 2013/0092630, and are performed by the software driven microprocessing unit of apparatus 200, with certain steps performed by the operator, as noted. For example, the apparatus 200 is switched on, and conducts self-calibration checks, including the checking of the peristaltic pumps, clamps, and sensors. Apparatus 200 then prompts the user to enter selected procedural parameters, such as the washing procedure to be performed, the amount of cell suspension to be washed, the number of washings to take place, etc. The operator may then select and enter the procedural parameters for the wash procedure, such that the wash procedure will be performed in accordance with the methodology described in greater detail below.

In keeping with the present disclosure the microprocessing unit will calculate the volume of wash solution needed for the procedure based on a "maximum output concentration" for the separator, defined as the maximum ratio of the volume of cellular material to the volume of the cell suspension that can be processed by the separator without losing cells of interest. The maximum output concentration for a spinning membrane separator of the type described above is a function of factors such as the configuration of the membrane, the pore size, and speed of rotation of the membrane. This may be determined or derived empirically for a particular spinner configuration, and pre-programmed into the microprocessor, or a value may be input by the system operator. For the purposes of illustration, it will be assumed that the maximum output concentration for the spinning membrane separator is 30% cellular material.

A "concentration ratio," defined as the ratio of the volume of the input to the separator to the output of the separator for the procedure, is determined. This value may be directly input into the controller by the system operator, or it may be automatically determined by the controller based on other operator input selections. For example, for frozen or thawed cell products, the system may use a concentration ratio of 2:1, while for fresh cell products the concentration ratio used by the system may be 10:1.

A "maximum input concentration" is determined as a function of the maximum output concentration and the concentration ratio. More specifically, the maximum input concentration is the maximum output concentration divided by the concentration ratio. During the washing procedure, washing solution is added to the cells to be washed in an amount so that the cellular concentration of the input to the separator in does not exceed the maximum input concentration. By way of example, if the maximum output concentration is 30% and fresh cell products are to be washed, for which the concentration ratio is 10:1, the maximum input concentration is 30%÷10=3%. Thus the volume of wash solution necessary for the procedure should be sufficient to dilute the suspension being input to the separator to a 3% cellular concentration, resulting in an output concentration that does not exceed 30%, and a container 135 containing at least this volume of wash solution should be connected to the disposable set 100 prior to the start of the wash procedure.

As can be appreciated, the volume of wash fluid in which the target cells may be suspended over the course of the washing procedure is variable. However, the number of the target cells to be processed is constant, if it is assumed that no target cells are lost during washing. In a typical washing procedure, target cells are flowed out of a container at a known flow rate, concentrated, and then flowed back into the container at a known flow rate (typically different from the outflow rate). Thus the value of the cellular concentration in the container is dynamic, but calculable, over the entire course of the washing procedure. The ability to calculate the volume of the wash fluid required prior to processing permits this information to be presented to the system operator, who can then connect bags with an appropriate capacity and/or prefilled volume prior to commencement of the washing procedure. Additionally, knowing the dilution and volumes needed for the entire procedure provide the ability to predict the amount of time required to process the biological fluid.

Returning to the steps of the wash procedure in common with the referenced co-pending application, apparatus 200 (through the controller) confirms the parameter entry and then prompts the operator to load the disposable set. The operator then loads the disposable set onto the panel of apparatus 200. In one exemplary embodiment, the disposable set may be the fluid circuit of FIG. 1. After installation of the disposable set, apparatus 200 confirms installation.

After the disposable set is mounted, apparatus 200 automatically checks to determine whether the disposable set is properly installed. After apparatus 200 determines that the disposable set is properly installed, the controller prompts the operator to connect the biological fluid and wash medium. The operator then connects the wash medium (such as, but not limited to saline) to the disposable set via a spike connector. The operator then connects source container 102 of the biological fluid or biological cell product (typically derived from an earlier, separate procedure) to the disposable set via a spike connector or sterile connection as previously described. In one embodiment, the source of biological fluid/cells may be apheresis-collected mononuclear cells.

After the source of biological fluid and wash medium are connected to the disposable set, the operator confirms that the solutions are connected. The device prompts the operator to take a cell suspension sample. The operator or the device then opens sampling assembly clamp to introduce fluid into the sample chamber of the sampling assembly. Once the sample chamber is sufficiently filled, it is then sealed and removed from the disposable circuit. The operator confirms that a sample has been taken. Following the removal of the sample chamber, the disposable fluid circuit is primed for the wash process. In one embodiment, the circuit may be primed with saline, although other bio-compatible aqueous solutions may also be used.

The controller of separation apparatus then commences the wash process. The biological cells to be washed are transferred from source container (e.g., 102 of FIG. 1) through the disposable set to the spinning membrane separator 101 via the operation of one or more peristaltic pumps 202, 204 and 206. Likewise, the wash medium is delivered from its container, through the disposable circuit to the spinning membrane separator 101. In a preferred embodiment, the original cells of the cell suspension are concentrated and/or collected in either an in-process bag (for further processing) or collected in a final product container 150, while supernatant is separated and removed to waste container 140. In a preferred embodiment, the process provides a final concentrated biological cell product 150 resuspended in approximately 200 mL of the wash (e.g., saline) solution with approximately a 2 log reduction of supernatant contents. If further washing or diluting of the cell suspension is necessary, the cell suspension in the in-process bag may be washed (a second time) with the same or different wash medium following the process outlined above. Prior to the conclusion of each wash cycle, the cell suspension volume or weight is measured and recorded. When the concentration of the cells to wash medium reaches an acceptable level the final product bag is filled. Once the desired volume of the final product is collected, the control and operation device prompts the operator to sample and seal the final product container. After sampling, the operator then seals and removes from the disposable circuit the washed cell suspension in the final product container 150.

The systems and methods described herein may also be effective in the washing of cells such as red blood cells and/or white blood cells. In one example of red cell washing, frozen red blood cells may be incubated within a rejuvenating solution such as Rejuvesol. The solution may be sterile docked or otherwise included in the closed system of the disposable processing sets of the type described above. Incubation occurs at approximately 37° C. within the closed system. The treated cells may then be washed with a washing solution such as saline, Adsol or E-Sol (the latter of which are red blood cell storage solutions and generally comprise dextrose, mannitol and a buffer) to reconstitute the red blood cells for subsequent storage and transfusion.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

It will be understood that the on-line dilution described above is not limited to the cell washing system described herein. For example, the pressure monitoring and on-line dilution system may also be used in any cell washing system including a cell washing system of the type described in International application PCT/US12/28522 filed Mar. 9, 2012 and incorporated by reference herein.

Thus, an improved method and system have been disclosed for the washing of biological cells. The description provided above is intended for illustrative purposes only and is not intended to limit the scope of the invention to any specific method, system, or apparatus, or device described herein.

The method has several aspects. In a first aspect, a method is provided for washing biological cells in which the separator has a predetermined maximum output concentration for the biological cells that are being washed. The method further includes determining the concentration ratio of the biological cells to be washed in the washing procedure and determining a maximum input concentration as a function of the maximum output concentration and the concentration ratio. Wash solution is then added to dilute said biological cells so that the maximum input concentration of the diluted biological cells entering the separator is not exceeded.

In another aspect, the method further comprises introducing diluted cells into the separator to separate the cells from the liquid medium and concentrate the cells. At least some of the concentrated cells are removed from the separator through a first outlet, and at least some of the separated liquid medium is removed from the separated through a second outlet.

Other aspects of the method include empirically deriving the maximum output concentration for the separator, and diluting the biological cells by either i) combining the biological cells with the wash solution and introducing the combination of cells and diluent into the separator, or ii) first introducing the wash solution into the separator followed by adding biological cells to the separator.

In further aspects of the method, the concentration ratio of the biological cells to be washed is from approximately 2:1 to 10:1. Additionally, the maximum input concentration is from approximately 3% to 15%. The biological cells may be either fresh cell products or frozen, thawed cell products. The biological cells may comprise red blood cells, and the wash solution may comprise a red blood cell additive solution.

In another aspect a system for processing biological fluids is provided in which the system comprises a fluid flow circuit including a container of biological fluid to be washed, a container of wash solution, and a separator having a relatively rotatable cylindrical housing, an internal member, and an inlet and first and second outlets. The cylindrical housing of the separator has an interior surface and the internal member has an exterior surface, the surfaces defining a gap therebetween. At least one of the surfaces includes a porous membrane for which a maximum output concentration that can be processed by the separator has been established. The system further comprises a programmable controller with a user interface, the controller being configured to perform the methods of the aspects set forth above.

In another aspect of the system, the porous membrane comprises pores ranging in size from approximately 0.8 µm to 30 µm and has a thickness of from approximately 10.0 µm to 50 µm. In addition, the porous membrane comprises polycarbonate.

The invention claimed is:

1. A method for washing a suspension comprising blood cells having a known cellular concentration to achieve a final volume of washed blood cells having a specified concentration with a fluid circuit comprising a spinning membrane separator including a porous membrane and for which a maximum output concentration of the blood cells to be washed that can be processed by the separator without loss of the blood cells has been established, the fluid circuit further comprising an in-process container and a final product container, the method comprising an initial wash cycle in which the suspension of blood cells to be washed is flowed from a source container to the spinning membrane separator for washing and washed, concentrated blood cells are flowed from the spinning membrane separator to the in-process container, and one or more intermediate wash cycles in which blood cells are flowed from the in-process container to the spinning membrane separator for further washing and concentration and washed, concentrated blood cells are flowed either back into the in-process container for further washing or to the final product container, the method further comprising:
   a) determining a concentration ratio of the blood cells to be washed for each cycle in the washing procedure;
   b) determining a maximum input concentration of the blood cells to be washed by dividing the maximum output concentration by the concentration ratio;
   c) determining a volume of wash solution to be used for washing the blood cells for each wash cycle as being a volume sufficient to dilute the cellular concentration of the blood cells to be washed to the maximum input concentration over the entire course for each wash cycle to determine a total volume of wash solution to be used for the wash procedure;
   d) attaching to the fluid circuit one or more wash solution containers holding at least the total volume of wash solution to be used for the wash procedure;
   e) drawing blood cells from either the source container in a first wash cycle or from the in-process container in an intermediate wash cycle;
   f) adding wash solution from the one or more wash solution containers to dilute the blood cells so that the cellular concentration of the blood cells in the spinning membrane separator does not exceed the maximum input concentration;
   g) introducing the diluted blood cells into the spinning membrane separator;
   h) separating said blood cells from at least some of said wash solution;
   i) concentrating said blood cells;

j) removing at least some of the concentrated blood cells from the spinning membrane separator through a first outlet to the in-process container;
k) removing at least some of said separated wash solution from the spinning membrane separator through a second outlet to a waste container;
l) continuously calculating the cellular concentration of the blood cells in the in-process container and comparing the determined cellular concentration to a cellular concentration specified for that wash cycle; and
m) if the cellular concentration of the blood cells is substantially the same as the cellular concentration specified for that wash cycle, then exiting that wash cycle; or
n) if the cellular concentration of the blood cells is not substantially the same as the cellular concentration specified for that wash cycle, then flowing the blood cells back to the spinning membrane separator and continuously adding wash solution in an amount that does not exceed the maximum input concentration based on the calculated cellular concentration of the blood cells in the in-process container.

2. The method of claim 1 further comprising if the cellular concentration of the blood cells is substantially the same as the cellular concentration specified for that wash cycle, the wash cycle is exited and the washed blood cells are transferred to the final product container.

3. The method of claim 1 further comprising if the cellular concentration of the blood cells is not substantially the same as the cellular concentration specified for that wash cycle, then continuing that wash cycle by returning to step e).

4. The method of claim 1 further comprising empirically deriving the maximum output concentration for the separator.

5. The method of claim 1 further comprising diluting said blood cells by combining said blood cells with said wash solution and introducing said combination of blood cells and wash solution into said separator.

6. The method of claim 1 comprising diluting said blood cells by first introducing said wash solution into said separator followed by adding blood cells to said separator.

7. The method of claim 1 wherein the concentration ratio of the blood cells to be washed is from 2:1 (for frozen, thawed blood cell products) to 10:1 (for fresh blood cell products).

8. The method of claim 1 wherein the maximum input concentration is from 3% (for fresh blood cell products) to 15% (for frozen, thawed blood cell products).

9. The method of claim 1 wherein the blood cells are fresh blood cell products.

10. The method of claim 1 wherein the blood cells are frozen, thawed blood cell products.

11. The method of claim 1 wherein the blood cells are red blood cells.

12. The method of claim 11 wherein the wash solution comprises a red blood cell additive solution comprising dextrose, mannitol and a buffer.

13. A system for processing biological fluids comprising:
a fluid flow circuit including a container of biological fluid to be washed, a container of wash solution, and a separator having a relatively rotatable cylindrical housing and an internal member, wherein said cylindrical housing has an interior surface and said internal member has an exterior surface, said surfaces defining a gap therebetween, wherein at least one of said surfaces includes a porous membrane and for which a maximum output concentration that can be processed by the separator has been established, the separator further comprising an inlet and first and second outlets; and
a programmable controller with a user interface, the controller being configured to perform the method of claim 1.

14. The system of claim 13 wherein the porous membrane comprises pores ranging in size from 0.8 μm to 30 μm and has a thickness of from 10.0 μm to 50 μm.

15. The system of claim 14 wherein the porous membrane comprises polycarbonate.

* * * * *